(12) United States Patent
Katakura et al.

(10) Patent No.: US 6,224,826 B1
(45) Date of Patent: May 1, 2001

(54) STERILIZING METHOD AND APPARATUS

(75) Inventors: Kageyoshi Katakura, Tokyo; Masahiro Kurihara; Kazuo Takei, both of Yokohama; Shinichiro Umemura, Hachioji; Kenichi Kawabata, Higashimatsuyama; Hiroshi Masuzawa, Machida, all of (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 09/270,846

(22) Filed: Mar. 18, 1999

(30) Foreign Application Priority Data

Mar. 19, 1998 (JP) .................................................. 10-069738

(51) Int. Cl.⁷ ....................................................... A61L 2/00
(52) U.S. Cl. ................ 422/20; 204/180.2; 261/DIG. 48; 366/15; 366/120; 422/128
(58) Field of Search ........................ 422/20, 128; 366/15, 366/120; 261/DIG. 48; 204/180.2

(56) References Cited

U.S. PATENT DOCUMENTS 3,607,675 * 9/1971 Haines .
4,202,740 * 5/1980 Stoner et al. .......................... 204/130
5,032,027 * 7/1991 Berliner, III ............................. 366/15
5,126,024 * 6/1992 Bonelli et al. ...................... 204/180.2

OTHER PUBLICATIONS

A handbook of ultrasonic technology Nikkan Kogyo Shinbunsha, pp. 856–859, (with translation of relevant portion). No date available.

* cited by examiner

Primary Examiner—Krisanne Thornton
(74) Attorney, Agent, or Firm—Mattingly, Stanger, & Malur, P.C.

(57) ABSTRACT

A method and apparatus for sterilizing water containing pathogen protozoa having shells in a simple manner without negative influencing the environment is disclosed. Ultrasonic waves are applied to drinking water to form fine cavitation bubbles which are used to destroy the shells of pathogenic protozoa. The residual chlorine in the drinking water along with an oxidizing action and effect of the ultrasonic wave, permit not only sterilization but also deodorization and decolorization.

13 Claims, 5 Drawing Sheets

STERILIZING METHOD AND APPARATUS

BACKGROUND OF THE INVENTION

The present invention relates to a sterilizing method and apparatus for sterilizing or eliminating pathogens living in water. More particularly, the invention is concerned with a sterilizing method and apparatus that are capable of safely sterilizing or eliminating pathogenic protozoa having a shell and other bacteria.

At present, the disinfection of water by utility companies is performed using chlorine. For sterilizing purposes, however, disinfection using chlorine is ineffective against pathogenic protozoa having a shell such as, for example, cryptosporidium.

The use of powerful chemicals may be effective in enhancing the sterilizing effect. In this case, however, even if the sterilizing effect is attained, there arises the problem of environmental pollution. Thus, without careful consideration, the use of such chemicals must be avoided.

U.S. Pat. No. 5,611,993 describes a method of sterilizing a continuous flow of wastewater containing bacteria which includes applying high frequency sound waves to the continuous flow of wastewater to cause cavitation in the wastewater. However, to the best of the present inventors' knowledge, sterilizing pathogenic protozoa having a shell such as, for example, cryptosporidium is not known in the prior art.

SUMMARY OF THE INVENTION

It is an object of the present invention to provide a sterilizing method and apparatus capable of easily disinfecting or sterilizing pathogenic protozoa having a shell such as, for example, cryptosporidium, without contaminating the environment.

For achieving the above-mentioned object, the present invention is provided with sterilizing apparatus for radiating ultrasonic waves to water for drinking to produce cavitation bubbles in the drinking water, thereby sterilizing pathogens living in water.

Not only sterilization but also deodorization and decolorization can be effected by using both an oxidizing effect with ultrasonic waves and chlorine remaining in tap water.

Another object is to provide a sterilizing apparatus and method that separates living bacteria and radiates ultrasonic waves to the living bacteria thereby enabling effective sterilization.

For achieving the above-mentioned object, the present invention is provided with a sterilizing apparatus including electrodes which apply a direct current field to a conduit having a water flowing path so as to collect living bacteria, a collection path for separating the collected living bacteria whose moving path has been changed by the direct current field, an ultrasonic radiator disposed on an outer peripheral side of the conduit to radiate ultrasonic waves to the separated living bacteria through the collection path, the ultrasonic waves having a sufficient intensity to generate cavitation bubbles, and a water flow direction controlling portion provided in the conduit to let the water flow so as to traverse ultrasonic wave surfaces formed by the ultrasonic radiator.

DETAILED DESCRIPTION OF THE PREFERRED EMBODIMENTS

Figure 1:
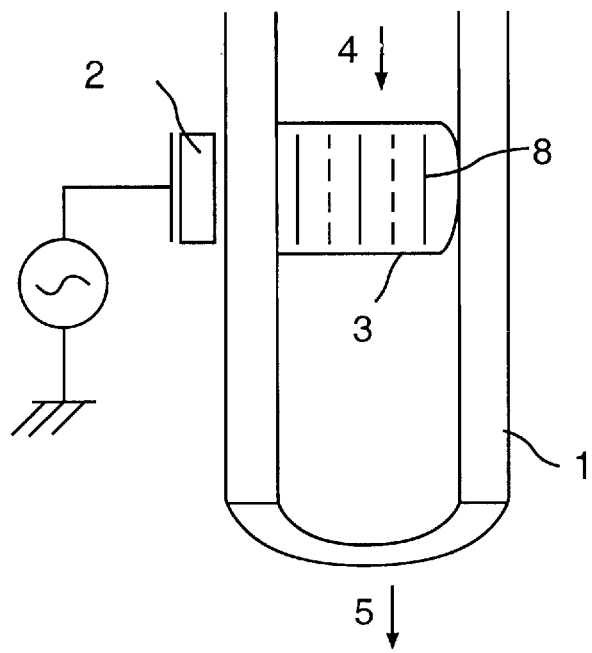
FIG. 1 illustrates a basic principle of a sterilizing apparatus according to an embodiment of the present invention.

Sterilizing actions using ultrasonic waves are classified, for example, into ones which utilize mechanical destruction using cavitation bubbles, ones which utilize thermal effect based on ultrasonic heating, and ones which utilize chemical effect based on an oxidizing action. In the present situation, according to the bacterium to be sterilized, it must be determined which method is to be adopted and an optimum design is made.

The present inventors have paid particular attention to the sterilization of pathogens (pathogenic protozoa) having a shell such as, for example, cryptosporidium. In this case, if the shell of the pathogen can be destroyed, the bacterium will die due to the residual chlorine in tap water. Having therefore considered that mechanical destruction is most effective, the present inventors have recognized that cavitation bubbles are an important factor.

The cavitation bubbles can be generated easily by the rotor blades of a pump. However, it is impossible to attain a sufficiently effective sterilization using cavitation bubbles. This is attributable to the mechanism of the sterilizing action using cavitation bubbles. More particularly, according to the sterilizing action using cavitation bubbles, it is presumed that bacteria present on the surfaces of cavitation bubbles will be destroyed due to collision with liquid molecules rushing in from opposite sides when the bubbles shrink and disappear. According to this destruction mechanism, the larger the bubble area, the more effective the sterilizing effect.

The size of a cavitation bubble formed by the rotor blades of a conventional pump is approximately 10 cm in radius, the area thereof is approximately 1000 $cm^2$ and the volume thereof is approximately 4000 $cm^3$. However, in the case of a cavitation bubble having a radius of 1 mm, its area is 1/10000 a bubble having a 10 cm radius. Therefore, 1,000,000 bubbles having a 1 mm radius are needed for obtaining the same volume as that obtained by one bubble with a 10 cm radius. This is because if the volume of bubbles having a 1 mm radius was the same as the volume of a bubble having a 10 cm radius, the surface area of the bubbles having a 1 mm radius would be 100 times that of the bubble having a 10 cm radius. Therefore, the technique for generating such fine cavitation bubbles is essential for efficient sterilization.

The diameter of a cavitation bubble formed by an ultrasonic wave is less than its wavelength because a sound pressure is generated in a negative portion of the waveform. Since ultrasonic waves of 7.5 kHz are 20 cm in wavelength, smaller bubbles are formed than the cavitation bubbles of 10 cm radius formed by the rotor blades of a conventional pump. Thus, if cavitation bubbles are formed using ultrasonic waves of a higher frequency, it becomes possible to perform efficient sterilization.

It is known that the oxidizing action of ultrasonic waves is weak at low power below 25 W with corresponding frequency of below 20 kHz (see page 858 of A Handbook of Ultrasonic Technology Nikkan Kogyo Shinbunsha (a newly revised edition)). Thus, if cavitation bubbles are generated by radiation of ultrasonic waves with a frequency above 20 kHz, it becomes possible to effect not only mechanical destruction of the bacterial shell by the cavitation bubbles but also decomposition and detoxification by an oxidizing action of bacterial contents and decolorization or deodorization of dissolved colorant due to decomposition of bacteria.

The oxidizing action of ultrasonic waves is particularly strong at a frequency above 500 kHz. That is, utilizing ultrasonic waves with a frequency above 500 kHz will bring about a particularly outstanding effect for such incidental purposes such as decolorization or deodorization, when the radiating time period is short.

FIG. 1 illustrates a sterilizing apparatus embodying the present invention. Reference numeral 1 denotes a water flow path in a water pipe or a conduit. Along a side of the water pipe is disposed an ultrasonic device which includes an ultrasonic radiator 2. The ultrasonic radiator 2, which is used to radiate ultrasonic waves to a portion of the water pipe, has a frequency which creates such ultrasonic wave surfaces 8 as illustrated in a portion of the water flow path. Drinking water fed from an incoming path 4 is sterilized by ultrasonic radiation while passing through an ultrasonic radiation area 3 and is then supplied for drinking through an outgoing path 5.

Due to interference of an ultrasonic sound field, sound pressure nodes such as that shown by the ultrasonic wave surfaces 8 are formed. Therefore, the bacteria passing through this portion pass through without being destroyed.

Figure 2:
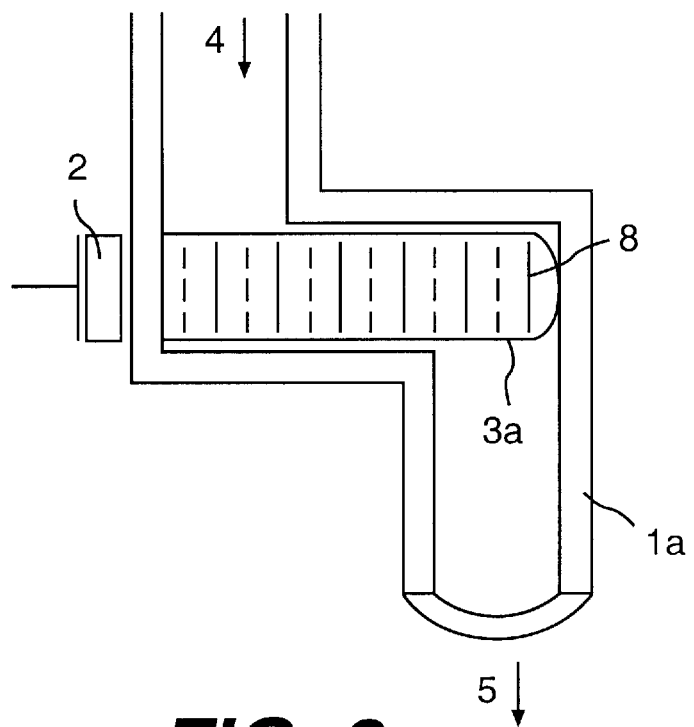
FIG. 2 illustrates another embodiment of FIG. 1.

Accordingly, by taking this problem into account, the present inventor has arrived at the embodiment shown in FIG. 2. According to this embodiment, a water flow path of a water pipe is formed in a crank shape, a wide portion of that crank shape is used as a radiation area 3a, and ultrasonic waves are radiated in a direction parallel to the water flowing direction. In FIG. 2, the water flow path changes directions by 90°, it should be understood that various other angles may also be effectively used.

Figure 3:
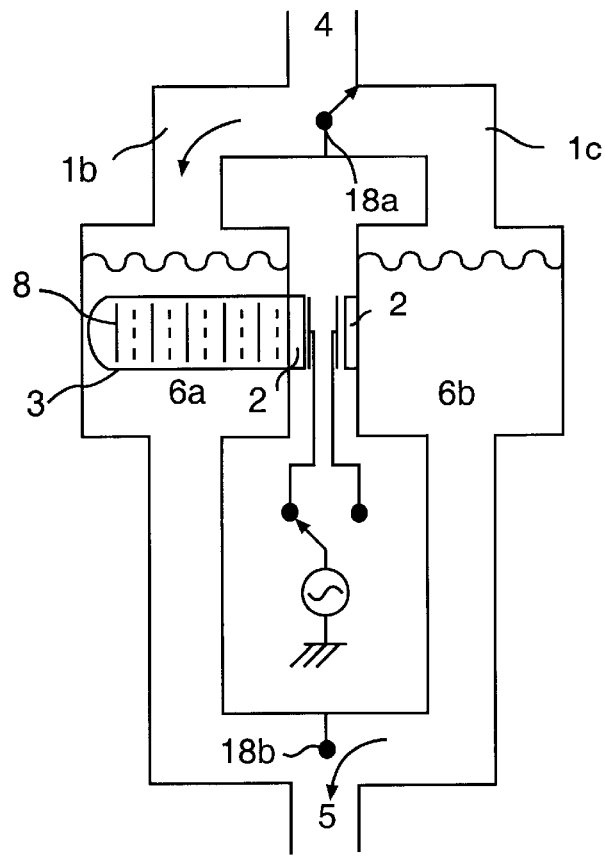
FIG. 3 illustrates another embodiment of the present invention.

FIG. 3 is a schematic diagram illustrating another embodiment of the present invention. Two water flow paths 1b and 1c are formed in a water pipe, and water tanks 6a and 6b having a diameter larger than the diameter of the water paths are disposed respectively in portions of the water paths. Ultrasonic radiators 2, are respectively disposed sideways of the water tanks, and they are driven selectively. Numeral 18a denotes a flow path change-over valve for directing water from an incoming path 4 to either the water flow path 1b or 1c. Numeral 18b denotes a flow path change-over valve for directing the water stored in either the water tank 6a or 6b to the outgoing path 5. For example, when the water flow path 1b is selected by the valve 18a, the valve 18b is changed over in the direction of selecting the water tank 6b. At this time, ultrasonic waves are radiated to the water tank 6a located on the water flow path 1b side to effect sterilization, while sterilized drinking water is directed to an outgoing path 5 from the other water tank 6b located on the water path 1c side which tank has already been sterilized.

Figure 4:
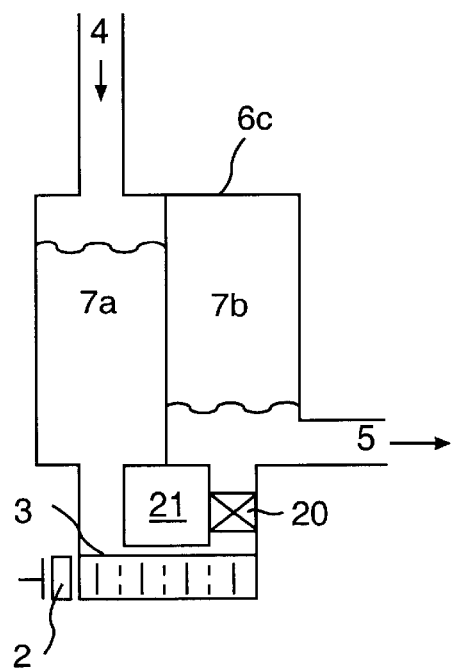
FIG. 4 illustrates an example of a water tank.

FIG. 4 shows an example in which the water tank 6a or 6b, shown in FIG. 3, has a plurality of tanks 7a (inflow portion) and 7b (outflow portion). The water stored in the water tank 6a is moved between the two tanks 7a and 7b by means of a pump 20 which is connected to a power source 21. An ultrasonic radiator 2 is disposed so that a radiation area 3 is formed at a bottom portion of each tank. According to this arrangement, the liquid that has been subjected to ultrasonic radiation is separated from the liquid that has not yet been subjected to the radiation, so that the sterilization can be done with even higher efficiency. The pump 20 can perform a reciprocating motion.

Figure 5:
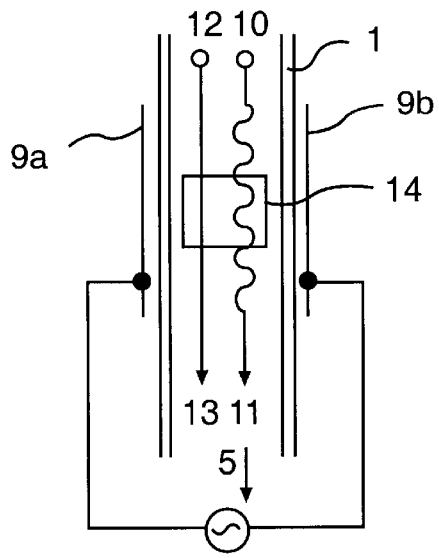
FIG. 5 illustrates how to detect living bacteria by using an electric field.

FIG. 5 is a diagram for explaining a technique for monitoring the state of sterilization in the drinking water sterilizing apparatus described above. Numerals 9a and 9b denote a pair of electrodes disposed on the outer periphery side of a flow path 1 in a water pipe. The electrodes 9a and 9b are used to apply an electric field to the flow path from an alternating current source. When an alternating current field is applied, a living bacterium 10 follows a meandering path as indicated by arrow 11 because its physiological activity keeps it charged electrically. On the other hand, a bacterial corpse 12 after ultrasonic destruction becomes neutral electrically because its physiological activity is lost, and follows linear path as indicated by arrow 13. If such a difference in reaction to the applied electric field is observed by means of a monitor 14 disposed in the water path, it becomes possible to check the presence of the living bacterium.

Figure 6:
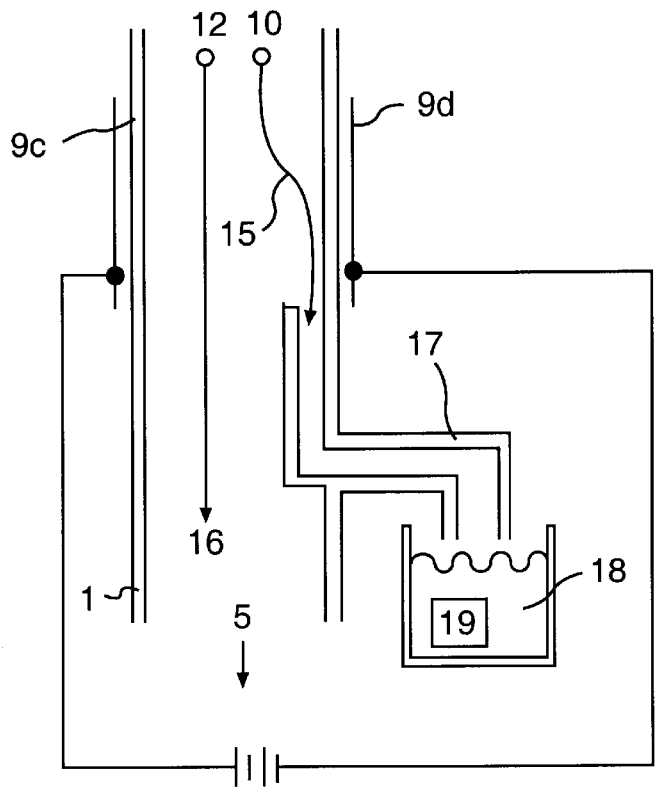
FIG. 6 illustrates how to separate living bacteria by using of a direct current field.

When a direct current field is applied to the electrodes 9c and 9d, a change in the path of movement occurs as indicated by arrow 15 in FIG. 6 because the living bacterium 10 is electrically charged due to its physiological activity. On the other hand, the destroyed bacterial corpse 12 is neutral electrically and follows a linear path as indicated by arrow 16. Thus, a collection path 17 for the separation and collection of bacteria is formed in the flow path of the water pipe from bacterial corpses, whereby living bacteria can be separated from bacterial corpses. The bacteria thus separated are cultivated in a cultivator 18 and then subjected to discrimination for the presence or absence of living bacteria in a discriminator 19. This makes it possible to improve the accuracy of determining the completion of sterilization. By terminating the radiation of the ultrasonic waves after making sure of such extermination of living bacteria, it is possible to obtain effective utilization of energy. If the electrodes 9c and 9d, as shown in FIG. 6, are connected to a DC power source and applied to the embodiments of FIGS. 2, 3, 4 and 5, more effective sterilization could be realized. Generally speaking, the number of pathogenic protozoa per liter of water is very small. Therefore, by collecting the pathogenic protozoa, efficiency is greatly improved.

Figure 7:
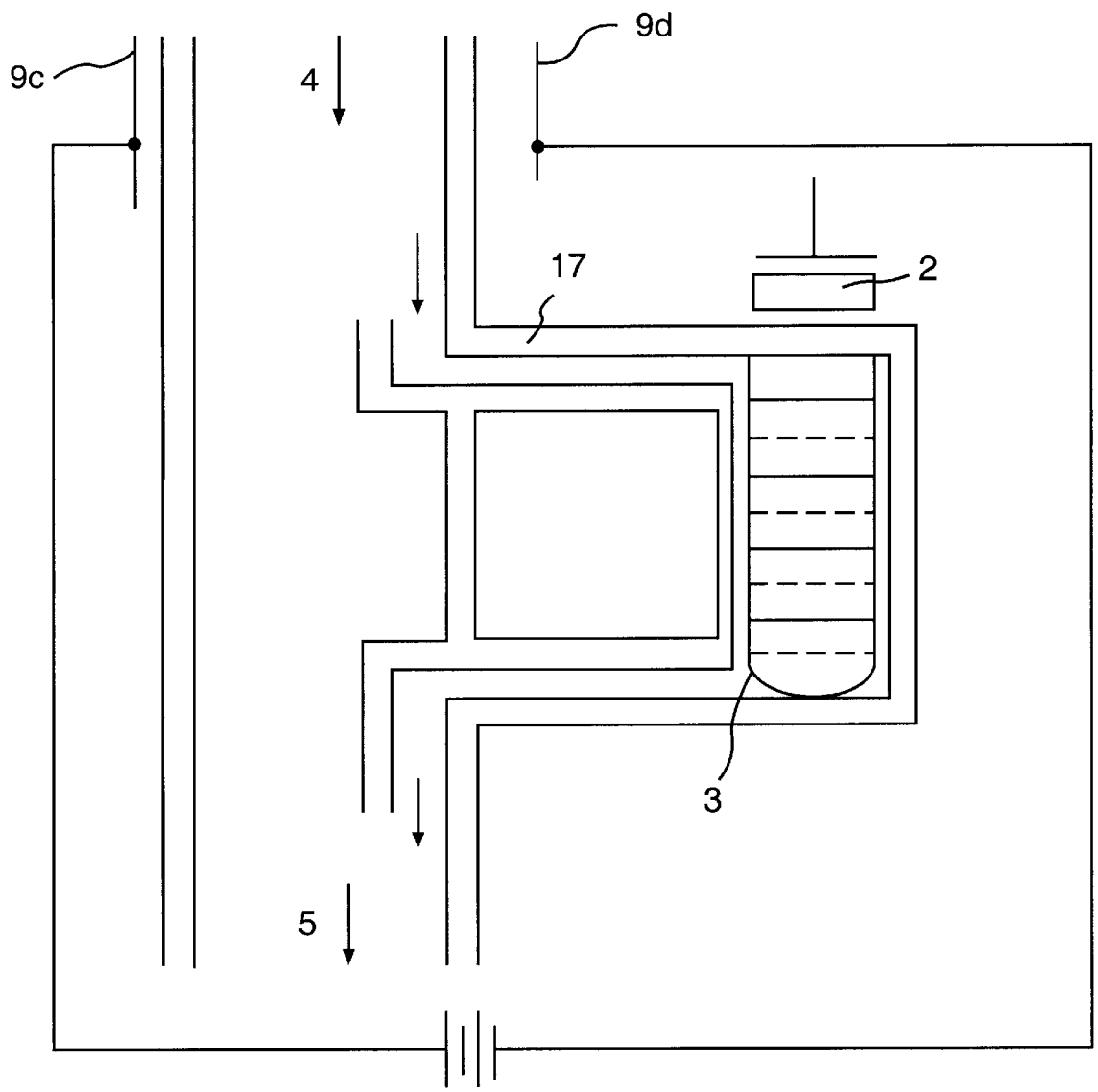
FIG. 7 illustrates an ultrasonic waves radiating structure capable of attaining a high efficiency by separation of living bacteria.

FIG. 7 shows an example of a combination between the ultrasonic sterilization technique shown in FIGS. 1 through 4 and the technique shown in FIG. 6. According to the construction illustrated in FIG. 7, an outwardly protruded, hollow portion is formed laterally from a flow path 1, and a collection path 17 is formed so that living bacteria are directed into the hollow portion by applying a direct current field as in FIG. 6. An ultrasonic radiator 2 is attached to a portion of the collection path 17, which contains living bacteria at a high concentration, in order to radiate ultrasonic waves to the flow path. This structure makes it possible to realize an efficient utilization of energy.

Figure 8:
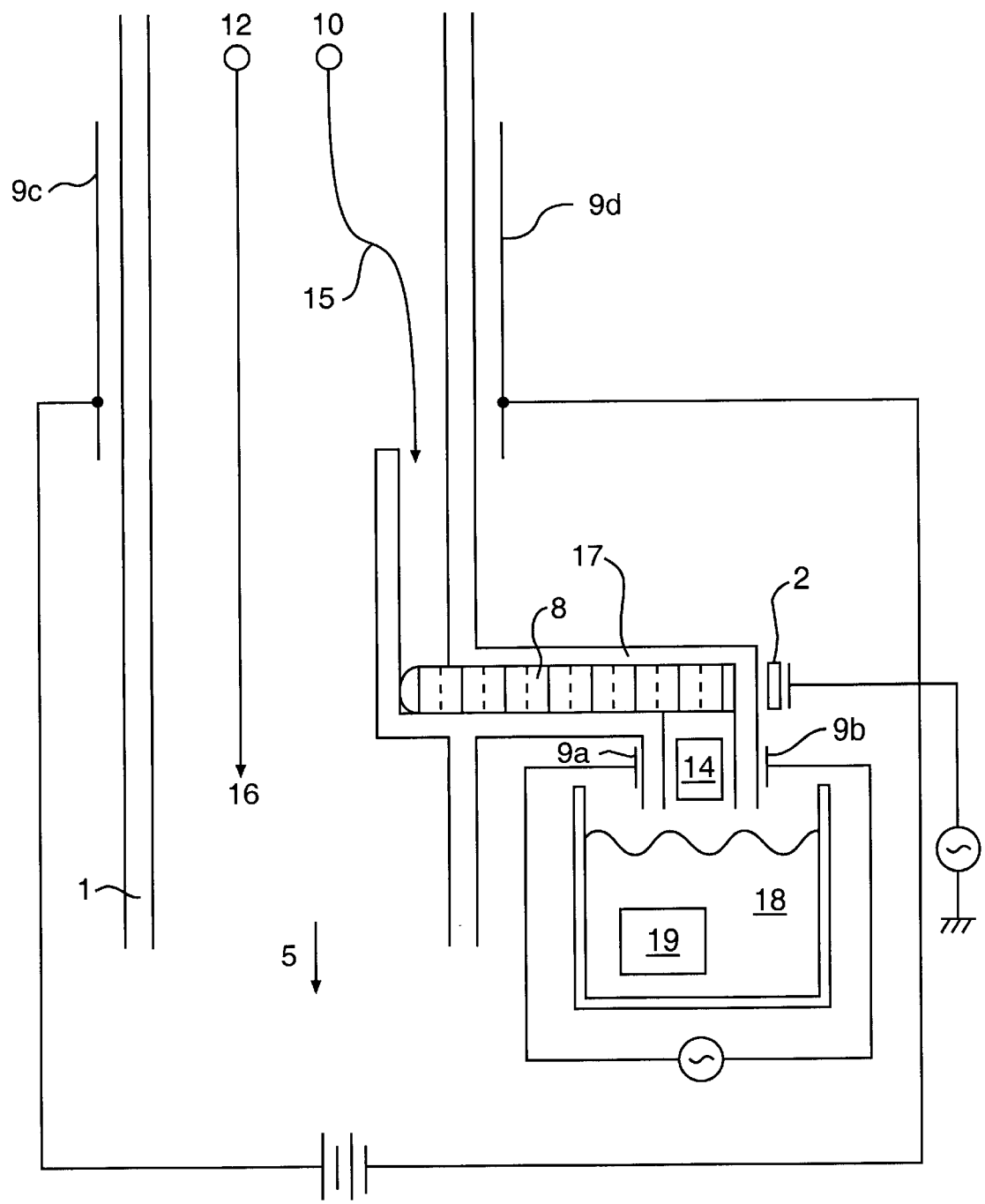
FIG. 8 illustrates another embodiment of the present invention.

FIG. 8 is also a diagram showing an example of a combination among the ultrasonic sterilizing techniques shown in FIGS. 1, 2, 5 and 6. The direct current field applied by the electrodes separate living bacteria from the bacterial corpses. The separated living bacteria are directed to the collection path, and radiated by the ultrasonic radiator 2, which is disposed adjacent the collection path so that the water flow direction traverses the ultrasonic wave surfaces. Electrodes 9a, 9b are used to apply an alternating field from an alternating current source to a portion of the collection path that is below the ultrasonic radiator 2. A monitor 14 is disposed at the alternating field in order to check for the presence of living bacteria. This structure increases efficiency, because, the living bacteria are separated from bacterial corpses, and are radiated for a sufficient period of time and with enough intensity in the collection path 17, which is different from the outgoing path 5. Furthermore, this structure makes it possible to check whether the processed water includes living bacteria. If it is necessary to do further processing, the water in the cultivator is radiated with ultrasonic waves.

According to the present invention described above, bacteria contained in drinking water can be sterilized in a simple manner without negatively influencing the environment.

While the present invention has been described above in conjunction with the preferred embodiments, one of ordinary skill in the art would be enabled by this disclosure to make various modifications to the preferred embodiments and still be within the scope and spirit of the present invention as defined in the appended claims.

What is claimed is:

1. A sterilizing apparatus comprising:
    electrodes which apply a direct current field to a conduit having a water flowing path so as to collect pathogenic protozoa having shells along a collection path;
    an ultrasonic radiator disposed on an outer peripheral side of the conduit to radiate ultrasonic waves to the collected pathogenic protozoa flowing through the collection path, the ultrasonic waves having sufficient intensity to generate cavitation bubbles; and
    a water flow direction controlling portion provided in the conduit to cause the water to flow so as to traverse ultrasonic wave surfaces formed by the ultrasonic radiator,
    wherein the ultrasonic radiator radiates ultrasonic waves having a frequency above 500 kHz.

2. The sterilizing apparatus according to claim 1, wherein the ultrasonic radiator is directly connected to the conduit.

3. The sterilizing apparatus according to claim 1,
    wherein the water flow direction controlling portion has a crank portion that is formed in the conduit to change a flowing direction of the water, and the ultrasonic radiator radiates the water in the crank portion so that the water flow is parallel to a direction in which the ultrasonic waves are radiated.

4. The sterilizing apparatus according to claim 1,
    wherein the water flow direction controlling portion has a water tank which has a larger radius than another portion of the water flow direction controlling portion, and
    wherein the ultrasonic radiator radiates the water in the water tank.

5. The sterilizing apparatus according to claim 1,
    wherein the water flow direction controlling portion has at least two flow paths, with water tanks being provided respectively in each of the flow paths,
    wherein the sterilizing apparatus further includes flow path change-over means provided respectively in an inlet portion and an outlet portion of the flow paths to open and close the inlet and outlet portion to alternatively, temporarily store water in one of the flow paths, and
    wherein the ultrasonic radiator is provided adjacent each of the water tanks and radiates the ultrasonic waves through water stored in the water tank located in the flow path in which water is being temporarily stored.

6. The sterilizing apparatus according to claim 1,
    wherein the water flow direction controlling portion is separated into an inflow portion into which water flows from an inlet and an outflow portion through which water flows out to an outlet, bottom portions of each of the inflow portion and the outflow portion being connected to one another to permit water to flow therebetween, and the ultrasonic radiator is disposed adjacent at least one of the bottom portions and radiates ultrasonic waves to the water in the bottom portions such that the water flowing direction in the bottom portions is parallel to a direction in which the ultrasonic waves are radiated.

7. The sterilizing apparatus according to claim 1, further including
    alternating electrodes, mounted on a peripheral side of the conduit, which apply an alternating current field to the water through the electrodes, and
    a monitor which, at the portion of the conduit where the electrodes are provided, monitors pathogenic protozoa whose path of movement has been changed by the alternating current field.

8. A sterilizing apparatus comprising:
    a conduit having a water flowing path;
    electrodes which are mounted on an outer side of the conduit and which apply a direct current field to the water through the electrodes in order to collect pathogenic protozoa having shells along a collection path;
    an ultrasonic radiator disposed on an outer side of the conduit to radiate ultrasonic waves to the water through the collection path, the ultrasonic waves having sufficient intensity to generate cavitation bubbles;
    a water flow direction controlling portion provided in the conduit to let the water flow so as to traverse ultrasonic wave surfaces formed by the ultrasonic radiator;
    alternating electrodes which apply an alternating current field to the water which has been radiated; and
    a monitor which monitors the pathogenic protozoa at a portion of the conduit where the alternating electrodes are provided,
    wherein the ultrasonic waves have a frequency above 500 kHz.

9. A sterilizing method comprising:
    providing a water flow direction controlling portion;
    applying a direct current field to a conduit having a water flowing path so as to collect pathogenic protozoa having shells into a collection path;
    separating the collected pathogenic protozoa whose path of movement has been changed by the direct current field; and
    radiating ultrasonic waves to the separated pathogenic protozoa, the ultrasonic waves having a sufficient intensity to generate cavitation bubbles thereby sterilizing the pathogen protozoa contained in the water, wherein the water flow direction controlling portion provided in the conduit lets the water flow so as to traverse ultrasonic wave surfaces formed by the ultrasonic radiator, and
    wherein the ultrasonic waves have a frequency above 500 kHz.

10. The sterilizing method according to claim 9, wherein the water flow direction controlling portion has a water tank, and wherein the step of radiating radiates to the water tank.

11. The sterilizing method according to claim 9, wherein the water flow direction controlling portion has at least two flow paths, with water tanks being provided respectively in each of the flow paths;

wherein before the step of applying, the method also comprises the step of:

providing flow path change-over means respectively in an inlet portion and outlet portion of the flow paths to open and close the inlet and outlet portions to alternatively, temporarily store water in one of the flow paths; and wherein the step of radiating radiates the ultrasonic waves through water stored in the water tank located in the flow path in which water is being temporarily stored.

12. The sterilizing method according to claim 10, wherein the water tank direction controlling portion is separated into an inflow portion into which water flows from an inlet and an outflow portion through which water flows out to an outlet, bottom portions of each of the inflow portion and the outflow portion being connected to one another to permit water to flow therebetween, and the ultrasonic radiator is disposed adjacent at least one of the bottom portions and radiates ultrasonic waves to the water in the bottom portions such that a water flowing direction in the, bottom portions is parallel to a direction in which the ultrasonic waves are radiated.

13. The sterilizing method according to claim 9, further comprising the steps of:

providing electrodes mounted on an outer peripheral portion of the conduit and which apply an alternating current field to the water flowing path, and monitoring, at the portion of the conduit where the electrodes are provided, pathogenic protozoa whose path of movement has been changed by the alternating current field.

* * * * *